United States Patent [19]

Masse et al.

[11] Patent Number: 4,739,750

[45] Date of Patent: Apr. 26, 1988

[54] RASP FOR PREPARING THE MEDULLARY CANAL OF A BONE FOR RECEIVING A PROTHESIS

[76] Inventors: André Masse, 21, rue Brizeux, 35000 Rennes; Christian Malet, 14, rue Sarrette, 75014 Paris, both of France

[21] Appl. No.: 887,822

[22] Filed: Jul. 21, 1986

[30] Foreign Application Priority Data

Jul. 19, 1985 [FR] France ............... 85 11209

[51] Int. Cl.$^4$ ............................................. A61F 5/04
[52] U.S. Cl. ........................... 128/92 VJ; 128/303 R
[58] Field of Search ............ 128/92 V, 92 VJ, 303 R, 128/305; 29/78 T

[56] References Cited

U.S. PATENT DOCUMENTS

| | | | |
|---|---|---|---|
| 272,648 | 2/1884 | Bolesky et al. | 128/92 VJ |
| 273,806 | 5/1884 | Bolesk et al. | 128/92 VJ |
| 3,740,779 | 6/1973 | Rubricuis | 128/303 |
| 3,760,473 | 9/1973 | Studdard | 29/78 |
| 3,835,843 | 9/1974 | Karman | 128/17 |
| 3,874,003 | 4/1975 | Moser et al. | 128/305 |
| 4,306,550 | 12/1981 | Forte | 128/92 |
| 4,350,151 | 9/1982 | Scott | 128/17 |
| 4,466,429 | 8/1984 | Loscher et al. | 128/92 E |
| 4,587,964 | 5/1986 | Walker et al. | 128/42 VJ |

FOREIGN PATENT DOCUMENTS 1079467 11/1954 France .
2547192 12/1984 France .

OTHER PUBLICATIONS

French Search Report

*Primary Examiner*—C. Fred Rosenbaum
*Assistant Examiner*—Mark F. Colosimo
*Attorney, Agent, or Firm*—Stevens, Davis, Miller & Mosher

[57] ABSTRACT

The rasp combines a handle (1) and a toothed blade (2) made up of two relatively movable parts (3, 4). The part (4) is moved transversely relative to the part (3) by means of a screw (5), thereby enabling a surgeon to modify the width of the blade (2) so that it matches the width of a prosthesis which is to be put into place.

Surgical equipment.

9 Claims, 2 Drawing Sheets

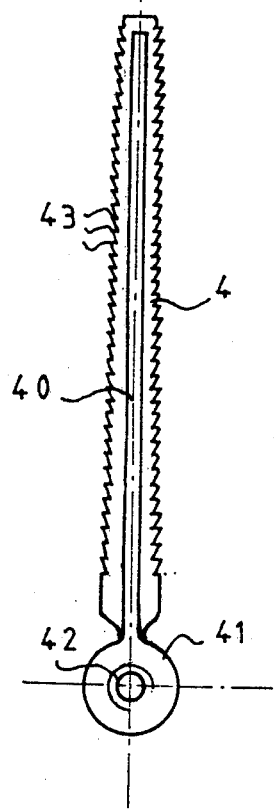
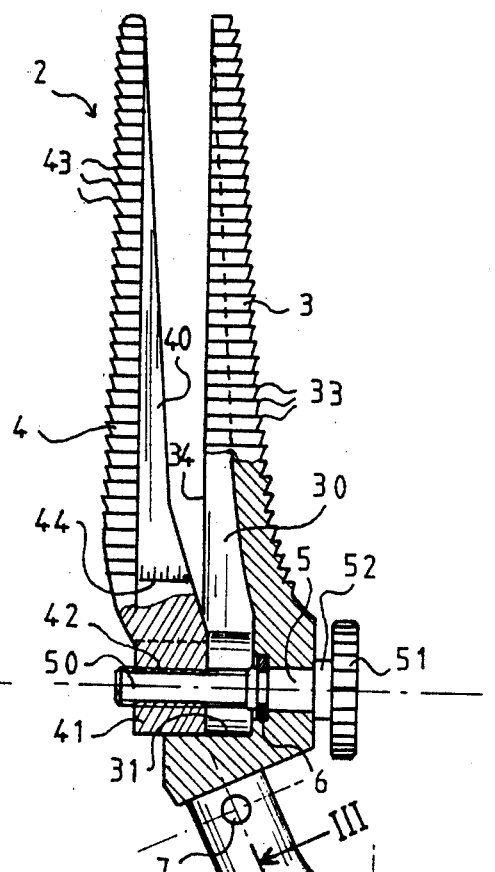
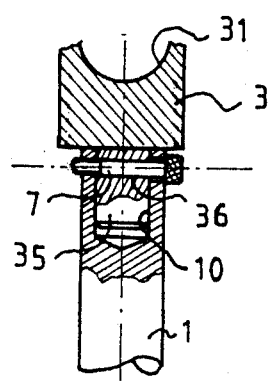
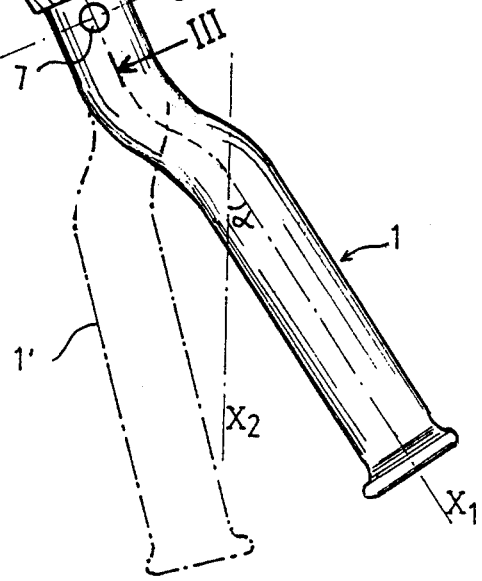

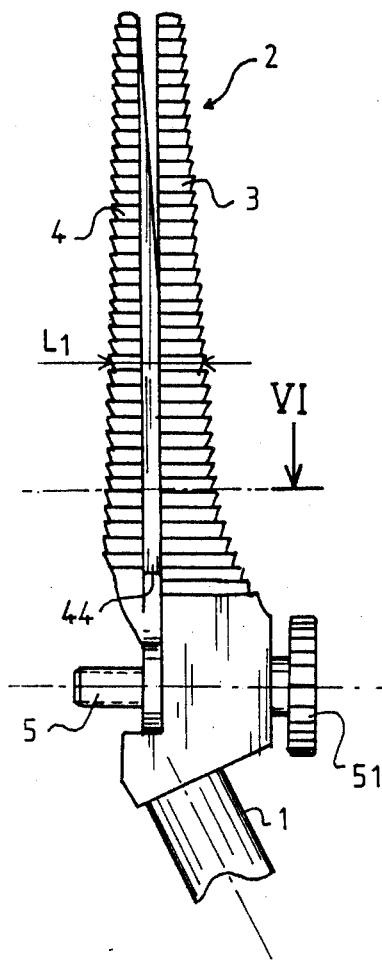
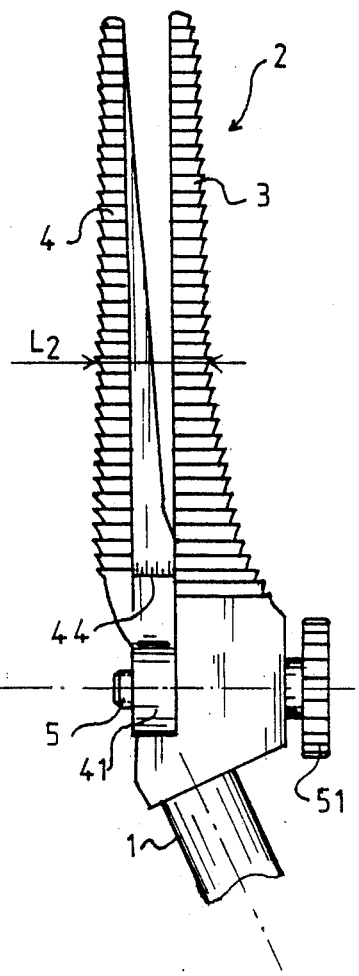
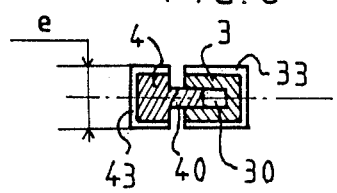

RASP FOR PREPARING THE MEDULLARY CANAL OF A BONE FOR RECEIVING A PROTHESIS

The present invention relates to a rasp for preparing the medullary canal of a bone for receiving a prosthesis.

Prior to inserting a prosthesis in a bone, and in particular a prosthesis in the top end of a femur, the surgeon must prepare the medullary cavity of the bone so as to give it a shape which is complementary to the shape of the prosthesis. This is done using a rasp which comprises a handle for gripping and a toothed blade whose shape corresponds to the shape of the prosthesis. The teeth on the blade are sharp, thereby enabling them to scrape away the surrounding spongy bone—like a file.

French published patent application No. FR-A-2 547 192 already describes a hollow femur rasp which comprises two complementary elongate portions which are separated, after use, in order to remove the bone debris which has collected inside the rasp.

There also exists medical instruments—called speculums—which are constituted by a pair of jaws capable of being separated from each other in order to dilate certain tissues; this type of instrument is described, for example, in U.S. Pat. No. 3,835,843 and belongs to different technical field than that of the invention.

It is known that the size and shape of a prosthesis for fixing to the end of a bone should be selected as a function of the mechanical and dimensional characteristics of the bone in question and on the type of lesion concerned. That is why a surgeon requires a large quantity of rasps of different shapes and sizes permanently available. Thus, for a given shape of hip prosthesis, it is necessary to have set of about 10 rasps, with middle portion widths which vary in millimeter steps over the range 10 mm up to about 20 mm. Such a large stock is naturally expensive and is difficult to manipulate.

The aim of the invention is to solve this problem by providing a rasp of the above-mentioned type and capable of preparing the medullary canals of bones for receiving prostheses of different sizes.

In accordance with the invention, this result is obtained by the fact that the active portion of the rasp in the form of a toothed blade is constituted by two complementary elongate portions which are movable relative to each other transversely relative to their longitudinal direction, with relative displacement of these two portions enabling the width of the blade to be varied.

In a preferred embodiment, one of the blade-constituting portions referred to as the fixed portion, is fixed to the handle, while the other portion is guided in translation to slide transversely relative to the fixed portion.

This sliding is advantageously assisted by means of co-operation between a guide tongue formed on one of the two portions and a groove formed in the other.

Relative displacement of the two portions may simply be provided by means of a screw. The screw may be guided, for example, in rotation while being fixed in translation in the fixed portion, with its threaded shank engaging in a tapped hole in the moving portion. The screw is preferably provided with a manual control head such as knurled disk, for example.

In accordance with a particularly advantageous characteristic of the invention, the rasp is advantageously provided with a graduated scale suitable for identifying the position of the two portions constituting the blade by displaying the blade width.

In accordance with another characteristic, the axis of the rasp handle is inclined relative to the longitudinal direction of the blade, thereby considerably facilitating rasping. In this case, the means for mounting the handle on the blade are advantageously adapted to engage the handle to occupy one or other of two positions angularly offset by 180° about its own axis.

Other characteristics and advantages of the invention appear from the description and the accompanying drawings which show a preferred embodiment.

FIG. 1 is a front view of the rasp in partial section.

FIG. 2 is a right-hand view of the moving blade portion of the FIG. 1 rasp.

FIG. 3 is a detailed view in section on a plane III of FIG. 1 showing means for mounting the handle to the blade.

FIGS. 4 and 5 are fragmentary front views of the rasp showing two different blade widths.

FIG. 6 is a section through the rasp blade on a horizontal plane VI of FIG. 4.

The rasp which is shown in the figures comprises two main portions: a handle 1 for enabling the surgeon to grasp the instrument in the hand, and an elongate toothed blade 2 whose thickness and width taper towards its point.

The length of the blade 2 is about 160 mm.

Its width is about 13 mm at its base and about 9 mm at its point.

The handle 1 is slightly bent in shape and the axis $X_1$ of its main portion (used for gripping) is inclined at an angle $\alpha$ relative to the longitudinal direction $X_2$ of the blade 2.

This angle $\alpha$ has a value of about 35°, for example.

The blade 2 is constituted by two portions: a fixed portion 3 fixed to the handle 1, and a moving portion 4. Both of the portions 3 and 4 bristle with sharp transverse teeth 33, 43 placed on their peripheries like scales. The moving portion 4 has a guide tongue 40 suitable for engaging in a complementary groove 30 formed in the fixed portion 3. After the tongue 40 has been engaged in the groove 30, the blade 2 formed by the two portions 3 and 4 have a contour similar to that of the prosthesis which it is to be put into place. In the example shown, the prosthesis is a hip prosthesis having a tapering point and a wider arcuate base.

The base of the fixed portion 3 has a quasi-cylindrical cavity 31 suitable for slidably receiving the base 41 of the moving portion, which base is in the form of a complementary peg. The peg 50 is displaced inside the cavity 31 by means of a screw 5. The screw is guided in translation along a bore 32 and is fixed in translation by a shoulder 52 and a spring clip 6 received in the base of the fixed blade portion 3. Its threaded shank 50 enters a complementary tapped hole 42 passing through the peg 41. This screw has a control head in the form of fluted or knurled disk making it easy to turn by hand.

The tongue 40 is provided, on at least one of its faces and preferably on both faces, with engraved marks constituting a graduated scale 44. The index for co-operating with this scale is constituted simply by the (rectilinear) inside edge 34 of the fixed portion 3.

The top of the handle 1 is provided with a bore 10 in which a cylindrical appendix 35 of the fixed portion 3 is received. The handle 1 is fixed to the appendix 5 by means of a knurled screw 7 which engages in a bore 36 passing diametrically through said appendix. Depending on the position given to the handle 1 relative to the bore 36, the handle may be given two different orientations which differ by 180° from each other, as can be seen in FIG. 1 where the second possible position is shown in dot-dashed lines and is referenced 1'.

In order to use the rasp, a surgeon begins by determining the width of the prosthesis that is to be used. Then, the surgeon uses the knurled disk 51 to rotate the screw 5 in one direction or the other in order to bring the two portions 3 and 4 closer together or to move them further apart. The graduated scale 44 provides information on the setting. FIGS. 4 and 5 show two settings at different widths, with respective widths L1 and L2 in the middle region of the rasp. The possible widths to which L1 and L2 may be set lie in a range which advantageously extends from 10 mm to 20 mm.

When the desired setting has been reached, the surgeon uses the instrument as an ordinary rasp in order to prepare the medullary canal for receiving the prosthesis. Depending on the operating technique used, the handle 1 may be positioned in one or other of its two positions which differ from each other by 180°.

The graduations on the scale 44 may be directly numbered as a function of the references of the various prostheses that may be used, or when using a prosthesis device in accordance with patent application No. 85 05348 filed Apr. 5, 1985, as a function of the references of the various modular bars which may be fitted on said device.

In order to cover all possible widths of a prosthesis of a given type, it is naturally possible to provide a single rasp having a large setting range. However, in some cases it may be advantageous to provide two rasps having smallersetting ranges, one being suitable for small sizes and the other for large sizes.

Naturally the invention is not limited to the embodiment described above merely by way of example. On the contrary, the invention covers all variants thereof.

Thus, in particular, the relative displacement between the two portions of the blade may be provided by means other than a screw and nut system, for example it may be provided by a rack and pinion system or by a sloping surface system (using the wedge effect).

The transverse teeth 33 and 43 may be replaced by spikes or other sharp projections suitable for providing the desired rasping action.

Finally, various rasp contours may naturally be provided as a function of the type of prosthesis concerned.

We claim:

1. A rasp for preparing the medullary canal of a bone for receiving a prosthesis, the rasp comprising:
   a handle; and
   a toothed blade having a width, said toothed blade is comprised of two complementary elongate portions having a longitudinal direction and means for permitting movement of said two portions relative to each other in a direction transverse to said longitudinal direction, and for enabling the width of the blade (2) to be varied.

2. A rasp according to claim 1, characterized in that one of the portions (3) constituting the blade (2), referred to as the fixed portion, is fixed to the handle (1), and in that the other portion (4) is guided in translation to slide transversely relative to the fixed portion (3).

3. A rasp according to claims 1 or 2, characterized in that one of the portions (4) constituting the blade (2) is provided with a guide tongue (40) which engages in a groove (30) of complementary shape provided in the other portion (3).

4. A rasp according to claim 3, characterized in that it includes a screw (5) suitable for providing relative displacement of the two portions (3) and (4).

5. A rasp according to claim 4 taken in combination, characterized in that the screw (5) is guided in rotation and fixed in translation in the fixed portion (3), with its threaded shank (50) engaging in a tapped hole (42) in the moving portion (4).

6. A rasp according to claim 5, characterized in that the screw (5) is provided with a manual control head, such as a knurled disk (51).

7. A rasp according to claim 1, characterized in that it is provided with a graduated scale (44) suitable for indicating the relative position of the two portions (3) and (4) constituting the blade (2) by displaying the blade width.

8. A rasp according to claim 1, characterized in that the axis ($X_1$) of its handle (1) is inclined relative to the longitudinal direction ($X_2$) of the blade (2).

9. A rasp according to claim 8, characterized in that the means for mounting the handle (1) on the blade (2) are adapted to enable the handle (1) to occupy one or other of two positions which are angularly offset by 180° about its own axis ($X_1$).

* * * * *